US012740959B2

(12) United States Patent
Walker et al.

(10) Patent No.: US 12,740,959 B2
(45) Date of Patent: Sep. 22, 2026

(54) METHODS FOR THE TREATMENT OF INFANTILE SPASMS USING MEDIUM CHAIN TRIGLYCERIDES

(71) Applicant: CERECIN AUSTRALIA PTY LIMITED, Melbourne (AU)

(72) Inventors: Judith Walker, Edinburgh (GB); Samuel T. Henderson, Golden, CO (US)

(73) Assignee: CERECIN AUSTRALIA PTY LIMITED, Melbourne (AU)

( * ) Notice: Subject to any disclaimer, the term of this patent is extended or adjusted under 35 U.S.C. 154(b) by 872 days.

(21) Appl. No.: 17/926,472

(22) PCT Filed: May 28, 2021

(86) PCT No.: PCT/US2021/034883

§ 371 (c)(1),
(2) Date: Nov. 18, 2022

(87) PCT Pub. No.: WO2021/243226

PCT Pub. Date: Dec. 2, 2021

(65) Prior Publication Data

US 2023/0181512 A1 Jun. 15, 2023

Related U.S. Application Data

(60) Provisional application No. 63/176,747, filed on Apr. 19, 2021, provisional application No. 63/032,111, filed on May 29, 2020.

(51) Int. Cl.
*A61K 31/23* (2006.01)
*A61P 25/08* (2006.01)

(52) U.S. Cl.
CPC .............. *A61K 31/23* (2013.01); *A61P 25/08* (2018.01)

(58) Field of Classification Search
CPC ...................................................... A61K 31/23
See application file for complete search history.

(56) References Cited

U.S. PATENT DOCUMENTS

| | | | |
|---|---|---|---|
| 7,807,718 | B2 | 10/2010 | Hashim et al. |
| 9,789,079 | B2 | 10/2017 | Pan et al. |
| 9,795,580 | B2 | 10/2017 | Weeber et al. |
| 10,562,839 | B2 | 2/2020 | Verdin et al. |
| 10,647,658 | B2 | 5/2020 | Verdin et al. |
| 10,668,041 | B2 | 6/2020 | Pan et al. |
| 10,889,538 | B2 | 1/2021 | Verdin et al. |
| 10,905,672 | B2 | 2/2021 | Cohen et al. |
| 10,945,975 | B2 | 3/2021 | D'Agostino et al. |
| 11,000,496 | B2 | 5/2021 | Cuenoud et al. |
| 11,224,581 | B2 | 1/2022 | Nakamura et al. |
| 11,331,279 | B2 | 5/2022 | Vangara et al. |
| 11,344,522 | B2 | 5/2022 | O'Donnell et al. |
| 11,351,138 | B2 | 6/2022 | Eaton et al. |
| 11,608,308 | B2 | 3/2023 | Verdin et al. |
| 2005/0228188 | A1* | 10/2005 | Sumida .................... A61Q 1/06 435/67 |
| 2006/0088517 | A1 | 4/2006 | Kriegler et al. |
| 2007/0197645 | A1 | 8/2007 | Martin et al. |
| 2007/0281892 | A1 | 12/2007 | Martin et al. |
| 2008/0058416 | A1 | 3/2008 | Greenwood et al. |
| 2008/0249173 | A1 | 10/2008 | Martin et al. |
| 2015/0342902 | A1 | 12/2015 | Vangara et al. |
| 2017/0348276 | A1 | 12/2017 | Bryson et al. |
| 2018/0028489 | A1 | 2/2018 | Vangara et al. |
| 2019/0091178 | A1* | 3/2019 | Abu-Izza ................ A23L 33/30 |
| 2019/0255003 | A1 | 8/2019 | D'Agostino et al. |
| 2019/0269699 | A1 | 9/2019 | Reddy et al. |
| 2020/0108040 | A1 | 4/2020 | Kunugi et al. |
| 2020/0147025 | A1* | 5/2020 | Eaton ...................... A23L 33/30 |
| 2020/0215013 | A1 | 7/2020 | Williams et al. |
| 2021/0205252 | A1 | 7/2021 | Gingrich et al. |
| 2022/0071942 | A1 | 3/2022 | Blanchard et al. |
| 2022/0152050 | A1 | 5/2022 | Reddy et al. |
| 2022/0160297 | A1 | 5/2022 | Wu et al. |
| 2022/0168256 | A1 | 6/2022 | Guenoud |
| 2022/0184022 | A1 | 6/2022 | Patin et al. |
| 2022/0273602 | A1 | 9/2022 | O'Donnell et al. |
| 2023/0021730 | A1 | 1/2023 | Cerne et al. |

FOREIGN PATENT DOCUMENTS

| | | |
|---|---|---|
| CN | 1972697 | 5/2007 |
| CN | 104736159 | 6/2015 |
| WO | WO 98/41201 | 9/1998 |
| WO | WO 2006/002121 | 1/2006 |
| WO | WO 2014/031792 | 2/2014 |
| WO | WO 2016/191651 | 12/2016 |
| WO | WO 2017/204986 | 11/2017 |
| WO | WO 2018/031748 | 2/2018 |
| WO | WO 2021/233796 | 11/2021 |
| WO | WO 2022/018094 | 1/2022 |
| WO | WO 2022/096637 | 5/2022 |
| WO | WO 2022/183292 | 9/2022 |
| WO | WO 2022/232106 | 11/2022 |

(Continued)

OTHER PUBLICATIONS

Hanifiha et al., "The efficacy of the ketogenic diet in improving seizures and eeg findings in patients with refractory infantile spasms," Iranian Journal of Child Neurology, 2022, 16(4), 45-54.*

(Continued)

*Primary Examiner* — Svetlana M Ivanova
(74) *Attorney, Agent, or Firm* — NORTON ROSE FULBRIGHT US LLP

(57) ABSTRACT

The present disclosure relates to methods for the treatment of Infantile Spasms and/or the prevention of spasms of Infantile spasms. The methods include administering compositions comprising at least one compound capable of elevating ketone body concentrations in a subject in need thereof (e.g., ketogenic compounds), administered in an amount effective for treatment of Infantile Spasms and or the prevention of spams of Infantile Spasms. In one embodiment, the composition includes medium chain triglycerides (MCT). The composition may be administered as an oral dosage forms, in particular, a nutritional drink comprising at least one compound capable of elevating ketone body concentrations in a subject.

13 Claims, 2 Drawing Sheets

(56) References Cited

FOREIGN PATENT DOCUMENTS

| | | |
|---|---|---|
| WO | WO 2022/242882 | 11/2022 |
| WO | WO 2022/242883 | 11/2022 |
| WO | WO 2022/246572 | 12/2022 |
| WO | WO 2023/001724 | 1/2023 |

OTHER PUBLICATIONS

Dressler et al., "Efficacy and tolerability of the ketogenic diet versus high-dose adrenocorticotropic hormone for infantile spasms: a single-center parallel-cohort randomized controlled trial," Epilepsia, 2019, 60(3), 441-451.*
Su et al., "SCN2A mutation in an infant presenting with migrating focal seizures and infantile spasm responsive to a ketogenic diet," Brain & Development 40 (2018) 724- 727.*
Liu et al., "Medium-chain triglyceride ketogenic diet, an effective treatment for drug-resistant epilepsy and a comparison with other ketogenic diets," Biomedical Journal 2013, 36(1), 9-15.*
Vandenberghe et al., "Tricaprylin Alone Increases Plasma Ketone Response More Than Coconut Oil or Other Medium-Chain Triglycerides: An Acute Crossover Study in Healthy Adults," Curr Dev Nutr 2017;1:1-5.*
Cantillon et al., Ketogenic drug tricaprilin (CER-0001) for the treatment of refractory infantile epileptic spasms: a phase 1/2a study, Frontiers in Pediatrics, 13:1575014, Feb. 20, 2026.*
"Medium Chain Triglycerides [Monograph]," Altern Med Rev. 2002; 7: 418-420.
Busner et al., "The clinical global impressions scale: applying a research tool in clinical practice," Psychiatry, 2007, (Edgmont (Pa.: Township)), 4(7), 28-37.
Buss et al., "Nonclinical safety and pharmacokinetics of miglyol 812: a medium chain triglyceride in exenatide once weekly suspension," Journal of Applied Toxicology: Jat, 2018, 38(10), 1293-1301.
Liu, "Medium-chain triglyceride (mct) ketogenic therapy," Epilepsia, 2008, 49, S8, 33-36.
Sampaio, "Ketogenic diet for epilepsy treatment," Arquivos De Neuro-Psiquiatria, 2016, 74(10), 842-848.
Sher et al., "Therapeutic efficacy of ACTH in symptomatic infantile spasms with hypsarrhythmia," Pediatric Neurology 1993, 9(6), 451-6.
Swift et al., "Medium-chain fatty acids: evidence for incorporation into chylomicron triglycerides in humans," The American Journal of Clinical Nutrition, 1990, 52(5), pp. 834-836.
Vandenplas et al., "Development of the brussels infant and toddler stool scale ('bitss'): protocol of the study," BMJ Open, 2017, 7(3).
Wheless, J.W., et al., Infantile spasms (West syndrome): update and resources for pediatricians and providers to share with parents. BMC Pediatr, 2012. 12: p. 108.
Kellaway, P., et al., Precise characterization and quantification of infantile spasms. Ann Neurol, 1979. 6(3): p. 214-8.
Riikonen, R., Long-term outcome of West syndrome: a study of adults with a history of infantile spasms. Epilepsia, 1996. 37(4): p. 367-72.
Watanabe, K., West syndrome: etiological and prognostic aspects. Brain Dev, 1998. 20(1): p. 1-8.
Marshall, C.R., et al., Infantile spasms is associated with deletion of the MAGI2 gene on chromosome 7q11.23-q21.11. Am J Hum Genet, 2008. 83(1): p. 106-11.
Michaud, J.L., et al., The genetic landscape of infantile spasms. Hum Mol Genet, 2014. 23(18): p. 4846-58.
Zhongshu, Z., et al., Clinical analysis of West syndrome associated with phenylketonuria. Brain Dev, 2001. 23(7): p. 552-7.
Stafstrom, C.E. and G.L. Holmes, Infantile spasms: criteria for an animal model. Int Rev Neurobiol, 2002. 49: p. 391-411.
Pellock, J.M., et al., Infantile spasms: a U.S. consensus report. Epilepsia, 2010. 51(10): p. 2175-89.
Scantlebury, M.H., et al., A model of symptomatic infantile spasms syndrome. Neurobiol Dis, 2010. 37(3): p. 604-12.
Cortez, M.A., et al., Infantile spasms and Down syndrome: a new animal model. Pediatr Res, 2009. 65(5): p. 499-503.
Baram, T.Z., et al., High-dose corticotropin (ACTH) versus prednisone for infantile spasms: a prospective, randomized, blinded study. Pediatrics, 1996. 97(3): p. 375-9.
Prezioso, G., et al., Efficacy of ketogenic diet for infantile spasms: A systematic review. Acta Neurol Scand, 2018. 137(1): p. 4-11.
Hrachovy, R.A., J.D. Frost, Jr., and D.G. Glaze, High-dose, long-duration versus low-dose, short-duration corticotropin therapy for infantile spasms. J Pediatr, 1994. 124(5 Pt 1): p. 803-6.
Lux, A.L., et al., The United Kingdom Infantile Spasms Study comparing vigabatrin with prednisolone or tetracosactide at 14 days: a multicentre, randomised controlled trial. Lancet, 2004. 364(9447): p. 1773-8.
Elterman, R.D., et al., Randomized trial of vigabatrin in patients with infantile spasms. Neurology, 2001. 57(8): p. 1416-21.
Hrachovy, R.A., et al., Double-blind study of ACTH vs prednisone therapy in infantile spasms. J Pediatr, 1983. 103(4): p. 641-5.
Eun, S.H., et al., Ketogenic diet for treatment of infantile spasms. Brain Dev, 2006. 28(9): p. 566-71.
Kossoff, E.H., et al., A case-control evaluation of the ketogenic diet versus ACTH for new-onset infantile spasms. Epilepsia, 2008. 49(9): p. 1504-9.
Hong, A.M., et al., Infantile spasms treated with the ketogenic diet: prospective single-center experience in 104 consecutive infants. Epilepsia, 2010. 51(8): p. 1403-7.
Caraballo, R., et al., Long-term follow-up of the ketogenic diet for refractory epilepsy: multicenter Argentinean experience in 216 pediatric patients. Seizure, 2011. 20(8): p. 640-5.
Numis, A.L., et al., The relationship of ketosis and growth to the efficacy of the ketogenic diet in infantile spasms. Epilepsy Res, 2011. 96(1-2): p. 172-5.
Li, B., et al., Effects of ketogenic diet on the clinical and electro-encephalographic features of children with drug therapy-resistant epilepsy. Exp Ther Med, 2013. 5(2): p. 611-615.
Lee, J., et al., Prognostic factors of infantile spasms: role of treatment options including a ketogenic diet. Brain Dev, 2013. 35(8): p. 821-6.
Pires, M.E., et al., Ketogenic diet for infantile spasms refractory to first-line treatments: an open prospective study. Epilepsy Res, 2013. 105(1-2): p. 189-94.
Kayyali, H.R., et al., Ketogenic diet efficacy in the treatment of intractable epileptic spasms. Pediatr Neurol, 2014. 50(3): p. 224-7.
Hirano, Y., et al., Ketogenic diet therapy can improve ACTH-resistant West syndrome in Japan. Brain Dev, 2015. 37(1): p. 18-22.
Hussain, S.A., et al., Limited efficacy of the ketogenic diet in the treatment of highly refractory epileptic spasms. Seizure, 2016. 35: p. 59-64.
O'Callaghan, F.J., et al., The effect of lead time to treatment and of age of onset on developmental outcome at 4 years in infantile spasms: evidence from the United Kingdom Infantile Spasms Study. Epilepsia, 2011. 52(7): p. 1359-64.
Go, C.Y., et al., Evidence-based guideline update: medical treatment of infantile spasms. Report of the Guideline Development Subcommittee of the American Academy of Neurology and the Practice Committee of the Child Neurology Society. Neurology, 2012. 78(24): p. 1974-80.
Groleau, V., et al., Long-term impact of the ketogenic diet on growth and resting energy expenditure in children with intractable epilepsy. Dev Med Child Neurol, 2014. 56(9): p. 898-904.
Shaw, D.M., et al., Exogenous Ketone Supplementation and Keto-Adaptation for Endurance Performance: Disentangling the Effects of Two Distinct Metabolic States. Sports Med, 2020. 50(4): p. 641-656.
Poff, A.M., A.P. Koutnik, and B. Egan, Nutritional Ketosis with Ketogenic Diets or Exogenous Ketones: Features, Convergence, and Divergence. Curr Sports Med Rep, 2020. 19(7): p. 251-259.
Sharman, M.J., et al., A ketogenic diet favorably affects serum biomarkers for cardiovascular disease in normal-weight men. J Nutr, 2002. 132(7): p. 1879-85.
Wiemer-Kruel A: "Ketogenic diets", Zeitschrift Fur Epileptologie, Springer Berlin Heidelberg, Berlin/Heidelberg, vol. 26, No. 3, Aug. 2, 2013 (Aug. 2, 2013), pp. 160-166.

(56) References Cited

OTHER PUBLICATIONS

Mackay et al., “Practice Parameter: Medical Treatment of Infantile Spasms,” Neurology, May 25, 2004, 62(1): 1668-1681.
Smith et al., “Infantile Spasms,” NCBI Bookshelf. A service of the National Library of Medicine, National Institutes of Health. StatPearls [Internet]. Treasure Island (FL): StatPearls Publishing; Mar. 10, 2023, 9 pages.

* cited by examiner

METHODS FOR THE TREATMENT OF INFANTILE SPASMS USING MEDIUM CHAIN TRIGLYCERIDES

RELATED APPLICATIONS

This application is a U.S. National Stage Application filed under 35 U.S.C. 371 of PCT Application No. PCT/US2021/034883, entitled "METHODS FOR THE TREATMENT OF INFANTILE SPASMS USING MEDIUM CHAIN TRIGLYCERIDES," filed on May 28, 2021, which claims benefit under 35 U.S.C. § 119 of U.S. Provisional Patent Application No. 63/032,111, filed May 29, 2020, entitled "MEDIUM CHAIN TRIGLYCERIDES FOR THE TREATMENT OF INFANTILE SPASMS", and U.S. Provisional Patent Application No. 63/176,747, filed Apr. 19, 2021, entitled "METHODS FOR THE TREATMENT OF INFANTILE SPASMS USING MEDIUM CHAIN TRIGLYCERIDES", the contents of which are each herein incorporated by reference in their entireties.

FIELD OF THE INVENTION

The disclosure relates to methods for the treatment of infantile spasms.

BACKGROUND OF THE INVENTION

Infantile spasms (IS), also known as West's syndrome, is a constellation of symptoms characterized by epileptic/infantile spasms, abnormal brain wave patterns called hypsarrhythmia and intellectual disability. Infantile spasms were first reported in The Lancet in 1841 by Dr. William West describing the condition in his 4-month-old son. IS is a unique and rare disorder with an incidence of 1.6 to 4.5 per 10,000 live births; this is roughly 2000 to 2500 new cases in the United States per year [1].

Onset of seizures usually occurs within the first year of life, with a peak age of onset of three to five months. 90% of children affected by IS present at less than 1 year of age with a peak incidence of 3 to 7 months. The spasms usually consist of sudden, generally bilateral, and symmetrical contractions of the neck, trunk, and extremities that are associated with a brief loss of consciousness. Less commonly, they consist of an extensor spasm of the legs and spine, or simple head nodding. Seizures often occur in clusters or runs; commonly 20 or so but as many as 100 spasms can occur in a single cluster, with each individual spasm lasting 1 to 2 seconds [2]. In most cases, they resolve by the age of three, although rarely they can persist up to 10 to 15 years of age.

IS is characterized by abnormal brain wave patterns called hypsarrhythmia. Hypsarrhythmia is an EEG pattern that is characterized by random, high-voltage spikes and slow waves. The typical appearance is more likely to be noted in earlier stages of infantile spasms.

IS is associated with several disorders such as cerebral palsy and Down syndrome. Some disorders, such as tuberous sclerosis and neuronal migration disorders, are discovered after the onset of spasms. Yet, in a significant minority of cases, the etiology remains unknown. Despite awareness of the condition for over 150 years, little progress has been made in our understanding of the pathophysiology of the condition, and treatment of the disorder has remained largely empirical.

The seizures are refractory to treatment with most conventional antiepileptic drugs. Although the spasms resolve with time, the long-term prognosis is poor. Many children develop other forms of severe epilepsy, and most (80% to 90%) have psychomotor retardation [3]. Some children have delayed development before the onset of their seizures as part of a predisposing condition, for example, Down syndrome. Nevertheless, even in these patients, further regression of development is often seen after the onset of spasms. The degree of psychomotor delay is severe in approximately 70% of children, placing a great burden on both caregivers and the health system.

Infantile spasms have been classified as either symptomatic and cryptogenic. Symptomatic IS is found in approximately 60% to 70% of cases and is assigned to patients with an "identified etiology and/or significant developmental delay at the time of spasm onset." [1]. Furthermore, symptomatic IS can be divided into three different groups (prenatal, perinatal and postnatal) based on the timing of when the insult occurred.

Prenatal cases with an identified etiology have been found to be associated with central nervous system (CNS) malformations, neurocutaneous disorders, chromosomal abnormalities, genetic mutations, inborn errors of metabolism, and congenital infections. The most common CNS malformation to occur in the prenatal period is cortical dysplasia and accounts for ~30% of IS cases. Other malformations that are associated with IS include: cerebral dysgenesis, lissencephaly, holoprosencephaly, and hemimegalencephaly [4]. The most common neurocutaneous disorder to be associated with infantile spasms is tuberous sclerosis complex (TSC) which accounts for about 10% to 30% of prenatal causes. About 68% of patients with TSC will have IS [4]. Other neurocutaneous disorders less commonly associated with IS include: nevus linearis sebaceous, incontinentia pegmenti, Ito syndrome, and neurofibromatosis type 1. The most common chromosomal abnormality to be associated with IS is Down syndrome. Up to 15% of prenatal causes of IS are attributed to chromosome abnormalities including 18q duplication, 7q duplication, deletion of MAGI2 gene on chromosome 7q11.23-q21.11 and partial 2p trisome [5]. Genetic mutations such as those encoding the forkhead protein G1, syntaxin-binding protein 1, calcium/calmodulin-dependent serine protein kinase, ALG13, pyridoxamine-5'-phosphate oxidase and adenylosuccinate lyase have been identified to be associated with IS [6]. The most common inborn error of metabolism to be associated with IS is Phenylketonuria (PKU). About 12 percent of patients with PKU will present with IS [7]. Congenital infections have also been associated with IS and include toxoplasmosis, syphilis, cytomegalovirus, and Zika virus [1].

Though prenatal factors account for the greatest proportion of causes of symptomatic IS, perinatal causes of IS include: hypoxic-ischemic encephalopathy, neonatal hypoglycemia and low birth weight [8]. Symptomatic postnatal cases are associated with traumatic injury, near drowning, tumors, and CNS infections which account for about 15% to 67% of cases of symptomatic IS [1].

Ten to 40% of patients with IS have no identifiable cause and are referred to as cryptogenic IS, and meet the following criteria: no other kind of seizures, a normal examination, a normal CT and MRI, recurrence of hypsarrhythmia between consecutive spasms of a cluster, and lack of any focal interictal or ictal EEG abnormalities. [1].

Due to the variety of insults that contribute to IS, it has been difficult to conclusively determine the pathophysiology. Yet, the variability of causes has led some to consider that there might be a common underlying mechanism. Stafstrom and Holmes proposed that IS "results from a nonspecific insult at a critical point in the ontogenetic development of the brain." [9]. There are two potential mechanisms that have garnered attention: increased excitability and loss of inhibition. One animal model that has been investigated is the stress related increase of neuropeptide corticotropin-releasing hormone (CRH) in limbic and brainstem regions in IS patients. CRH causes seizures in developing rodents and ACTH suppresses the synthesis of CRH, which may be a mechanism for the efficacy of this stress hormone in IS (for overview see [10]). Models related to the loss of inhibition common pathway include the triple hit model [11], the TTX model, and the Ts65D mouse model [12].

In 2010 an IS consensus group provided guidelines for the treatment of IS with the goal of improving patient outcomes [10]. The guidelines presented the importance of first-line therapy, and EEG evaluation to determine treatment effectiveness. The group also emphasized that early detection of IS is critical, to improve neurodevelopmental outcomes, particularly in cryptogenic cases [10].

The first line treatment for IS is hormonal therapy with Adrenocorticotropic hormone (ACTH). Typically, two different dosing regimens are used, a low dose or a high dose. The low dose normally consists of ACTH dosed at 20 to 30 units per day intramuscularly (IM) with reevaluation in 2 weeks, increasing to 40 units per day if spasms or hypsarrhythmia persist. The high dose consists of ACTH dosed at 75 units/m2 IM twice daily for 2 weeks; this is followed by a taper for an additional 2 weeks. For both dosing regimens if relapse occurs a second course for 4 to 6 weeks is administered. The typical time to cessation of spasms is expected to be 7 to 12 days and ACTH can be quite effective [8]. For example, Baram et al. evaluated a high-dose natural ACTH (150 IU/m2/day given twice daily) administered over a short duration (i.e., 2 weeks, followed by taper as follows: 30 IU/m2 in the morning 3 days, 15 IU/m2 in the morning 3 days, 10 IU/m2 in the morning 3 days, and then 10 IU/m2 every other morning for 6 days), 87% of subjects responded with both clinical cessation of spasms and abolition of hypsarrhythmia on EEG [13]. See Table 1 for a list of studies using ACTH and outcomes.

Another candidate for first line therapy for IS is vigabatrin. Vigabatrin is a GABA-transaminase inhibitor resulting in increased GABA in the CNS [8]. Vigabatrin dosing is typically initiated at 50 mg/kg per day and can be raised to 100 mg/kg per day. The typical length of treatment with vigabatrin is 6 to 9 months and the time to cessation of spasms is from 12 to 35 days [14]. See Table 1 for a list of studies using vigabatrin and outcomes.

Corticosteroids have also been used in the treatment of IS. In some studies, prednisone has been shown effective at dose is 2 mg/kg per day for a 6-week course. See Table 1 for a list of studies using prednisone and outcomes.

A ketogenic diet (KD) can be considered a second line treatment for IS. If ACTH or Vigabatrin prove ineffective, often a KD is initiated in IS. The KD is a high-fat, adequate-protein, low-carbohydrate diet. The most common type of KD is the "classic KD", in which the macronutrient content is restricted to a 4:1 or 3:1 fat to non-fat ratio. In 2017, Prezioso et al. conducted a review of the use of ketogenic diets in infantile spasms. The review found that 116 of 345 patients (33.62%) were free from spasms within 6 months of follow-up. Long term results were also available in a subset of studies and 40 of 169 (23.7%) remained seizure free 12 to 24 months later [15]. See Table 1 for a list of studies using KD and outcomes.

TABLE 1

IS Treatments

| Agent | N | Dose* | % of patient spasms stopped | Reference |
|---|---|---|---|---|
| ACTH | 24 | 20-20 IU/day | 58 | [16] |
| ACTH | 26 | 150 IU/m2/day | 50 | Hrachovy, 1994 #681} |
| ACTH | 15 | 150 IU/m2/day divided B.I.D. | 93 | [13] |
| ACTH (synthetic) | 25 | 40-60 IU (0.5-0.75 mg) alternate days | 76 | [17] |
| VGB | 75 | 18-36 mg/kg/day | 11 | [18] |
| VGB | 67 | 100-148 mg/kg/day | 36 | [18] |
| VGB | 52 | 100-150 mg/kg/day | 54 | [17] |
| Prednisone | 12 | 2 mg/kg/day | 33 | [19] |
| Prednisolone | 30 | 40-60 mg/day | 70 | [17] |
| Ketogenic diet | 43 | 3-4:1 | 53.5 | [20] |
| Ketogenic diet | 13 | 3-4:1 | 61 | [21] |
| Ketogenic diet | 104 | 3-4:1 | 36.5 | [22] |
| Ketogenic diet | 12 | 3-4:1 | 41.6 | [23] |
| Ketogenic diet | 26 | 3-4:1 | 34.6 | [24] |
| Ketogenic diet | 16 | 4:1 | 56.2 | [25] |
| Ketogenic diet | 14 | NS | 50 | [26] |
| Ketogenic diet | 17 | 3-4:1 | 64.7 | [27] |
| Ketogenic diet | 20 | 3-3.5:1 | 16.6 | [28] |
| Ketogenic diet | 6 | 3-4:1 | 16.7 | [29] |
| Ketogenic diet | 22 | 3-4:1 | 13.6 | [30] |

*For ketogenic diet ratio represents fat:non-fat in the diet, NS = not stated

It is a widely accepted view that earlier diagnosis, along with quicker control of the spasms, would improve the prognosis of IS patients [31]. However, IS is refractory to most conventional antiepileptic drugs. In addition, both ACTH and vigabatrin are not always effective and have potentially severe side effects [14]. ACTH treatment is associated with a number of serious adverse event (AEs)

including "hypertension, immune suppression, infection, electrolyte imbalances, GI disturbances, ocular opacities, hypertrophic cardiomyopathy, cerebral atrophy and growth impairment." [32]. Because of these side effects the low dose, short-term therapy is recommended. Vigabatrin is also associated with a number of AEs including sedation, irritability, insomnia and hypotonia. Importantly, vigabatrin can cause serious visual field defects that are permanent and persist even with discontinuation of the drug [1]. Ketogenic diets generally show a low incidence of AEs, but can result in reduced linear growth status resulting from long term use of KD in infants [33].

Accordingly, more effective and safe treatments are needed for IS.

SUMMARY OF THE INVENTION

Figure 1A:
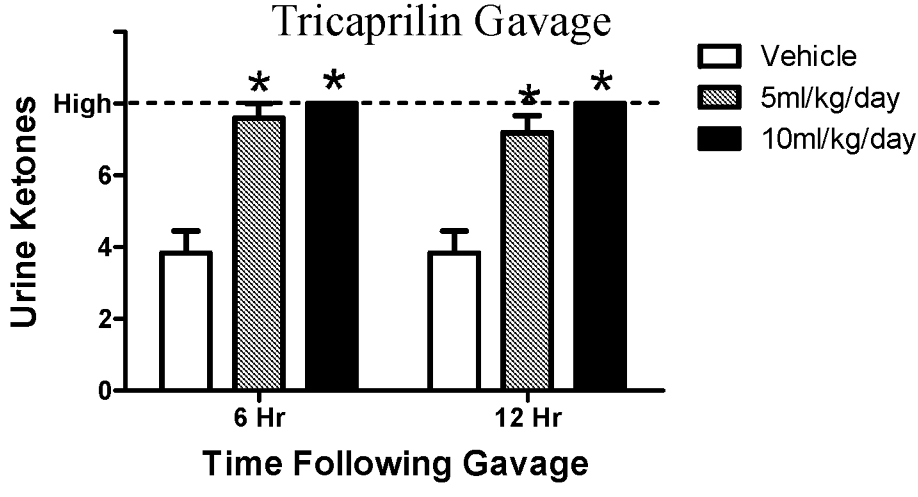
FIGS. 1A and 1B illustrate urinary ketone levels in response to the administration of an exemplary MCT, tricaprilin, according to embodiments of the disclosure. Tricaprilin led to elevation in urine ketone levels after both oral gavage (FIG. 1A) and feeding in milk (FIG. 1B). Units are mmol/L.

The present disclosure relates to a method for the treatment of Infantile Spasms and/or the prevention of spasms of Infantile Spasms in a subject in need thereof. In certain embodiments, the method comprises administering an effective amount of a composition comprising a compound capable of elevating ketone body concentrations in the body of a subject in need thereof.

In some embodiments, the composition may be administered in an amount effect to treat Infantile Spasms and/or prevent spasms of Infantile Spasm in a subject in need thereof. In some embodiments, the composition is administered in an amount effective to reduce spasms of Infantile Spasm in a subject in need thereof by at least 50%, when compared to no treatment. In other embodiments, the composition is administered in an amount effective to reduce spasms of Infantile Spasm in a subject in need thereof by at least 75%, when compared to no treatment.

In certain embodiments, the compound capable of elevating ketone body concentrations is a medium chain triglyceride (MCT). In certain embodiments, the composition is an emulsion comprising at least one MCT. In certain embodiments, the MCT may be tricaprilin.

In certain embodiments, the composition may be administered orally or intravenously. In certain embodiments, the composition may be administered orally as a nutritional supplement.

DETAILED DESCRIPTION OF THE INVENTION

The current disclosure describes a solution to the problem of ineffective treatments that are associated with serious side effects in the treatment of Infantile Spasms (IS). In certain aspects, the present disclosure relates the novel finding that the exogenous induction of ketosis can treat IS. In certain embodiments, it is shown that medium chain triglycerides (MCTs), and in particular tricaprilin, can treat IS. MCTs are triacylglycerols wherein the fatty acids are 5-12 carbons in length. In the case of tricaprilin, greater than 95%, 96%, 97%, 98% or 99%, or 100% of the fatty acids are octanoic acid comprised of 8 carbons (C8).

From the description herein, a number of advantages of the disclosure for treating infantile spasms and preventing spasms in infantile spasms will be evident:

(a) Current treatments for infantile spasms are not completely effective and are associated with serious side effects. The methods of the disclosure provide a simple and safe method to treat the condition.

(b) Increased blood levels of ketone bodies can be achieved by administration of a composition or regimen rich in ketogenic compositions such as medium chain triglycerides, e.g., tricaprilin.

(c) Many ketogenic compounds, such as medium chain triglycerides, can be infused intravenously into patients or administered orally.

(d) Levels of ketone bodies can be easily measured in urine or blood by commercially available products (e.g., Ketostix®, Bayer, Inc.).

Without intending to be limited by theory, ketogenic diets are not equivalent to the exogenous induction of ketosis by use of ketogenic agents such as tricaprilin, these two strategies are not equivalent as they exert two distinct metabolic states [34, 35]. Ketogenic diets are typically defined by the amount of fat consumed to the combined amount of carbohydrate and protein. Ketogenic diets typically use ratios of fat: carbohydrate+protein of 3:1 or 4:1. In practice, KDs limit carbohydrate (CHO) to less than 50 g of per day or <5% of energy intake, 15-20% of energy intake from protein and 75-80% of energy intake from fat. The ketogenic diets that have been used in the treatment of IS are all described as 3-4:1.

Due to the restrictive nature of macronutrient content of KDs, they exert a broad range of metabolic changes in patient. Because KDs limit carbohydrate and the ability to synthesize glucose from gluconeogenesis from amino acids, it shifts the metabolism primarily fat use as fuel. This metabolic shift results in many significant metabolic changes that are not evident from the exogenous induction of ketosis. Human subjects put on a ketogenic diet for 6 weeks demonstrate significant lowering of insulin (−34.2%), triglycerides (−33.0), and VLDL (−29.4%), all indicating a significant shift toward fat metabolism [36]. The exogenous induction of ketosis by the administration of ketogenic agents does not have these metabolic effects and instead simply increases the presence of ketone bodies in circulation and in the case of tricaprilin, increases the amount of octanoic acid in circulation. Note, while ketogenic diets also increase free fatty acids in circulation, they are not octanoic acid, and instead they are long chain fatty acids [35].

In a first aspect, the present disclosure provides a method for treating IS and/or preventing the occurrence of spasms in IS, in a subject in need thereof, the method comprising administering an effective amount of a composition comprising at least one compound capable of elevating ketone body concentrations in the body of a subject (e.g., a human subject), e.g., medium chain triglycerides (MCTs), to a subject in need thereof. In accordance with aspects of the disclosure, the compositions of the disclosure may be administered in a dosage effective to increase blood ketone bodies to a level which treats IS and/or prevents the occurrence of spasms in IS.

In some embodiments, the composition is administered in an amount effective to reduce spasms of Infantile Spasm in a subject in need thereof by at least 50%, at least 55%, at least 60%, at least 65%, at least 70%, at least 75%, at least 80%, at least 85%, at least 90%, at least 95%, at least 98%, at least 99%, etc., when compared to no treatment.

Therapeutically effective amounts of the therapeutic agents can be any amount or dose sufficient to bring about the desired effect and depend, in part, on the severity and stage of the condition, the size and condition of the patient, as well as other factors readily known to those skilled in the art. Generally, an effective amount is an amount effective to either (1) reduce the symptoms of the disease sought to be treated or (2) induce a change relevant to treating the disease sought to be treated. The dosages can be given as a single dose, or as several doses, for example, divided over the course of several weeks, as discussed elsewhere herein. Appropriate dosages of all of these compounds can be determined by one of skill in the art.

In all embodiments, compositions comprising at least one compound that is capable of elevating ketone body concentrations may be used in connection with the methods for treating IS and/or preventing spasms of IS. In one embodiment, the compositions useful in connection with the methods of the disclosure result in elevating ketone concentrations in the body of a subject, and may be administered in an amount that is effective to induce hyperketonemia. Such compounds are also collectively referred to as ketone body precursor compounds or ketogenic compounds. Such compounds include, for example, MCTs, MCFAs, and prodrugs, metabolic precursors, etc., of ketone bodies.

In one embodiment, the compound capable of elevating ketone body concentrations in the body include one or more prodrugs, which can be metabolically converted to the subject compounds by the recipient host. As used herein, a prodrug is a compound that exhibits pharmacological activity after undergoing a chemical transformation in the body. A prodrug can also be referred to as a metabolic precursor if the conversion of the prodrug directly results in the formation of a ketone body. MCTs and MCFAs must be first oxidized to acetyl-CoA, then undergo several steps before being synthesized into ketone bodies. A wide variety of prodrug formulations are known in the art. For example, prodrug bonds may be hydrolyzable, such as esters or anhydrides, or enzymatically biodegradable, such as amides.

In one embodiment, the compositions useful in connection with the methods of the disclosure may increase the circulating concentration of at least one type of ketone body in the subject. In one embodiment, the circulating ketone body is D-beta-hydroxybutyrate. The amount of circulating ketone body can be measured at a number of times post administration, and in one embodiment, is measured at a time predicted to be near the peak concentration in the blood, but can also be measured before or after the predicted peak blood concentration level. Measured amounts at these off-peak times are then optionally adjusted to reflect the predicted level at the predicted peak time. In one embodiment, the predicted peak time is at about two hours. Peak circulating blood level and timing can vary depending on factors known to those of skill in the art, including individual digestive rates, co-ingestion or pre- or post-ingestion of foods, drinks, etc., as known to one of skill in the art. In one embodiment, the peak blood level reached of D-beta-hydroxybutyrate is between about 0.05 millimolar (mM) to about 50 mM. Another way to determine whether blood levels of D-beta-hydroxybutyrate are raised to about 0.05 to about 50 mM is by measurement of D-beta-hydroxybutyrate urinary excretion a range in the range of about 5 mg/dL to about 160 mg/dL. In other embodiments, the peak blood level is raised to about 0.1 to about 40 mM, from about 0.1 to about 20 mM, from about 0.1 to about 10 mM, to about 0.1 to about 5 mM, more preferably raised to about 0.15 to about 2 mM, from about 0.15 to about 0.3 mM, although variations will necessarily occur depending on the formulation and host, for example, as discussed above. In other embodiments, the peak blood level reached of D-beta-hydroxybutyrate will be at least about 0.05 mM, at least about 0.1 mM, at least about 0.15 mM, at least about 0.2 mM, at least about 0.5 mM, at least about 1 mM, at least about 1.5 mM, at least about 2 mM, at least about 2.5 mM, at least about 3 mM, at least about 4 mM, at least about 5 mM, at least about 10 mM, at least about 15 mM, at least about 20 mM, at least about 30 mM, at least about 40 mM, and at least about 50 mM.

As used herein, and discussed elsewhere herein, MCTs of this disclosure are represented by the following formula:

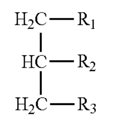

wherein R1, R2, and R3 are independently selected from the group consisting of a fatty acid residue esterified to a glycerol backbone having 5-12 carbons in the carbon backbone (C5 to C12 fatty acids), a saturated fatty acid residue esterified to a glycerol backbone having 5-12 carbons in the carbon backbone (C5 to C12 fatty acids), an unsaturated fatty acid residue esterified to a glycerol backbone having 5-12 carbons in the carbon backbone (C5 to C12 fatty acids), and derivatives of any of the foregoing.

In some embodiments, R1, R2, and R3 are fatty acids containing a six-carbon backbone (tri-C6:0). Tri-C6:0 MCT are absorbed very rapidly by the gastrointestinal tract in a number of animal model systems. The high rate of absorption results in rapid perfusion of the liver, and a potent ketogenic response. In another embodiment, the method comprises the use of MCT wherein R1, R2, and R3 are fatty acids containing an seven-carbon backbone (tri-C7:0). In another embodiment, the method comprises the use of MCT wherein R1, R2, and R3 are fatty acids containing an eight-carbon backbone (tri-C8:0). In another embodiment, the method comprises the use of MCT wherein R1, R2, and R3 are fatty acids containing a ten-carbon backbone (tri-C10:0). In another embodiment, the method comprises the use of MCT wherein R1, R2, and R3 are a mixture of C8:0 and C10:0 fatty acids. In another embodiment, the method comprises the use of MCT wherein R1, R2 and R3 are a mixture of C6:0, C8:0, C10:0, and C12:0 fatty acids.

In another embodiment, mixtures of MCTs may be used in connection with the methods of the disclosure. For example, in one embodiment, one MCT is comprised of R1, R2, and R3 wherein the fatty acids contain a ten-carbon backbone (tri-C10:0) and another MCT wherein R1, R2, and R3 are comprised of an eight-carbon backbone (tri-C8:0). In another embodiment, one MCT is comprised of R1, R2, and R3 wherein the fatty acids contain a eight-carbon backbone (tri-C8:0) and another MCT wherein R1, R2, and R3 are comprised of an six-carbon backbone (tri-C6:0). In another embodiment, one MCT is comprised of R1, R2, and R3 wherein the fatty acids contain a ten-carbon backbone (tri-C10:0) and another MCT wherein R1, R2, and R3 are comprised of a six-carbon backbone (tri-C6: 0).

In another embodiment, greater than 95% of R1, R2 and R3 carbon chains of the MCT are 8 carbons in length. In yet another embodiment, the R1, R2, and R3 carbon chains are 6-carbon or 10-carbon chains. In another embodiment, 50% of the R1, R2 and R3 carbon chains of the MCT are 8 carbons in length and about 50% of the R1, R2 and R3 carbon chains of the MCT are about 10 carbons in length.

In another embodiment, medium chain fatty acids (MCFA) of 5, 6, 7 8, 9, 10, 11 and 12 carbon chain length or mixtures of the above, may be used in connection with the methods of the disclosure.

The lipid compounds, e.g., MCTs or MCFAs, useful in the methods of the disclosure may be prepared by any process known in the art, such as direct esterification, rearrangement, fractionation, transesterification, or the like. By way of example, sources of the MCT include any suitable source, semi-synthetic, synthetic or natural. Examples of natural sources of MCT include plant sources such as coconuts and coconut oil, palm kernels and palm kernel oils, and animal sources such as milk from any of a variety of species, e.g., goats. Additionally, utilization of MCT can be increased by emulsification. Emulsification of lipids increases the surface area for action by lipases, resulting in more rapid hydrolysis and release of MCFA. Methods for emulsification of these triglycerides are well known to those skilled in the art.

In other embodiments, ketone body precursor compounds may be used in connection with the methods of the disclosure. Ketone body precursor compounds useful in connection with the present disclosure include any compounds that are capable of directly elevating ketone body concentrations in the body of a mammal, e.g., a patient, and may be determined by one of skill in the art. These compounds can mimic the effect of increasing oxidation of fatty acids and include but are not limited to the ketone bodies, D-μ-hydroxybutyrate and acetoacetate, and metabolic precursors of these. The term metabolic precursor, used herein, can refer to compounds that comprise 1,3 butane diol, acetoacetyl or D-β-hydroxybutyrate moieties such as acetoacetyl-1-1,3-butane diol, acetoacetyl-D-β-hydroxybutyrate, and acetoacetylglycerol. Esters of any such compound with monohydric, dihydric or trihydric alcohols are also useful in connection with the methods of disclosure. Metabolic precursors also include polyesters of D-β-hydroxybutyrate, and acetoacetate esters of D-β-hydroxybutyrate. Polyesters of D-β-hydroxybutyrate include oligomers of this polymer designed to be readily digestible and/or metabolized by humans or mammals. These preferably are of 2 to 100 repeats long, typically 2 to 20 repeats long, and most conveniently from 3 to 10 repeats long. Examples of poly D-β-hydroxybutyrate or terminally oxidized poly-D-β-hydroxybutyrate esters useable as ketone body precursors are given below:

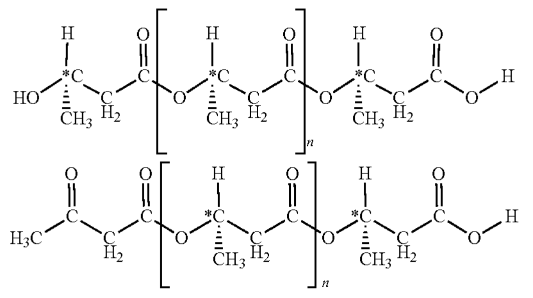

-continued

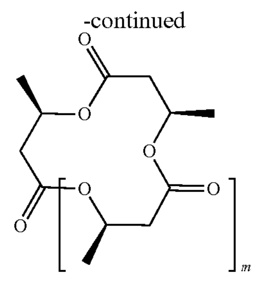

In each case, n is selected such that the polymer or oligomer is readily metabolized on administration to a human or mammal body to provide elevated ketone body levels in blood. Values of n are integers of 0 to 1,000, more preferably 0 to 200, still more preferably 1 to 50, most preferably 1 to 20, particularly conveniently being from 3 to 5. In each case m is an integer of 1 or more, a complex thereof with one or more cations or a salt thereof for use in therapy or nutrition. Examples of cations and typical physiological salts are described herein, and additionally include sodium, potassium, magnesium, calcium, each balanced by a physiological counter-ion forming a salt complex, L-lysine, L-arginine, methyl glutamine, and others known to those skilled in the art.

Other ketone body precursor compounds useful for treating infantile spasms include esters of polyhydric alcohols, 3-hydroxyacid esters and glycerol esters, as described more fully herein.

As used herein, "derivative" refers to a compound or portion of a compound that is derived from or is theoretically derivable from a parent compound; The term "hydroxyl group" is represented by the formula —OH; the term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below; the term "ester" is represented by the formula —OC(O)R, where R can be an alkyl, alkenyl, alkynyl, aryl, aralkyl, cycloalkyl, halogenated alkyl, or heterocycloalkyl group, as defined below; the term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms; the term "alkenyl group" is defined as a hydrocarbon group of 2 to 24 carbon atoms and structural formula containing at least one carbon-carbon double bond; the term "alkynyl group" is defined as a hydrocarbon group of 2 to 24 carbon atoms and a structural formula containing at least one carbon-carbon triple bond; the term "halogenated alkyl group" is defined as an alkyl group as defined above with one or more hydrogen atoms present on these groups substituted with a halogen (F, Cl, Br, I); the term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous; the term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms; the term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted; the term "aralkyl" is defined as an aryl group having an alkyl group, as defined above, attached to the aryl group. An example of an aralkyl group is a benzyl group; "esterification" refers to the reaction of an alcohol with a carboxylic acid or a carboxylic acid derivative to give an ester; "transesterification" refers to the reaction of an ester with an alcohol to form a new ester compound. The term "3-hydroxybutyrate" is used interchangeably with the term "3-hydroxybutyric acid."

In one embodiment, a compound capable of elevating ketone body concentrations includes compounds according to formula:

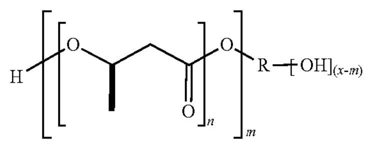

wherein R is a polyhydric alcohol residue; n, m and x represent integers; and m is less than or equal to x.

Physiologically compatible alcohols suitable for forming esters with (R)-3-hydroxybutyrate and derivatives thereof include monohydric and polyhydric alcohols. Esters of polyhydric alcohols deliver a higher density of (R)-3-hydroxybutyrate equivalents per equivalent of (R)-3-hydroxybutyrate derivative using shorter (R)-3-hydroxybutyrate oligomers. Shorter oligomers generally are more readily hydrolyzed to give elevated concentrations of (R)-3-hydroxybutyrate in blood. Examples of polyhydric alcohols suitable for preparing such esters include carbohydrates and carbohydrate derivatives, such as carbohydrate alcohols, examples of carbohydrates include, without limitation, altrose, arabinose, dextrose, erythrose, fructose, galactose, glucose, gulose, idose, lactose, lyxose, mannose, ribose, sucrose, talose, threose, xylose and the like. Additional examples of carbohydrates useful for preparing (R)-3-hydroxybutyrate derivatives include amino derivatives, such as galactosamine, glucosamine and mannosamine, including N-acetyl derivatives, such as N-acetylglucosamine and the like. Examples of carbohydrates also include carbohydrate derivatives, such as alkyl glycosides. Examples of carbohydrate alcohols include, without limitation, glycerol, mannitol, ribitol, sorbitol, threitol, xylitol and the like. The enantiomers of the above-listed carbohydrates and carbohydrate alcohols also can be used to prepare (R)-3-hydroxybutyrate derivatives according to the above formula.

Embodiments include compounds where n is from 1 to about 100; wherein x is from 1 to about 20; wherein m is from 1 to about 20. One embodiment includes a compound wherein R is (R)-1,3-butanediol.

In another embodiment, compounds capable of elevating ketone body concentrations include compounds of the formula:

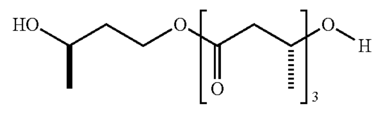

and also

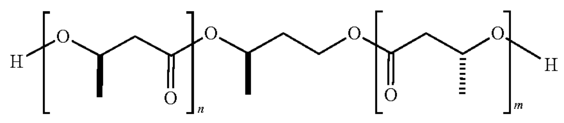

where n and m independently are integers from 1 to about 100. In some embodiments, n and m are the same; n and m are different; and wherein n and m are 3. In addition, compounds capable of elevating ketone body concentrations include ester compounds of R-3-hydroxybutyrate according to the formula:

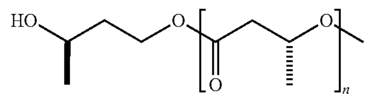

wherein n is an integer from 1 to about 100. In one embodiment, n is 3.

Other compounds capable of elevating ketone body levels include 3-hydroxyacids. The compositions include 3-hydroxyacids, linear or cyclic oligomers thereof, esters of the 3-hydroxyacids or oligomers, derivatives of 3-hydroxyacids, and combinations thereof. In one embodiment, the compositions include the cyclic macrolide of R-3-hydroxyacids containing 3, 4, or 5 monomeric subunits. 3-hydroxyacids include 3-hydroxybutyric acid, 3-hydroxyvaleric acid, 3-hydroxyhexanoic acid and 3-hydroxyheptanoic acid. In some embodiments, the length of the oligomer must be such that the derivative has a suitable digestion rate for sustained release of monomer. In another embodiment, the cyclic trimer (triolide) is used in a combination with other cyclic oligolides or linear esters and/or mixtures of both.

The general formula for 3-hydroxyacids is:

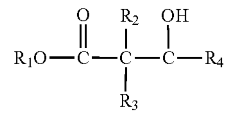

wherein R1 is selected from hydrogen, methyl, alkyl, alkenyl, aryl, arylalkyl, heteroalkyl, heteroaryl, thiol, disulfide, ether, thiol ether, amine, amide, halogen. R2 and R3 are independently selected from hydrogen, methyl, alkyl, alkenyl, aryl, arylalkyl, heteroalkyl, heteroaryl, thiol, disulfide, ether, thiol ether, amine, amide, halogen, hydroxy, ester, nitrogen-substituted radicals, and/or oxygen-substituted radicals. R4 is selected from hydrogen, alkyl, alkenyl, aryl, arylalkyl, heteroalkyl, heteroaryl, thiol, disulfide, ether, thiol ether, amine, amide, halogen, hydroxy, ester, nitrogen-substituted radicals, and/or oxygen-substituted radicals. Further, when R4 is not hydrogen or a halogen, R3 can be a direct bond to and R4 can be methyl.

Other compounds capable of elevating ketone body levels include glycerol esters, namely, not readily water-soluble glycerides of at least one keto or hydroxy acid, having the formula:

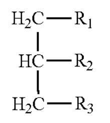

wherein two or three of the groups R1, R2 and R3 independently of each other, are one or more of the groups acetoacetate, alpha-ketopropionate, beta-hydroxybutyrate and alpha-hydroxypropionate, and when only two of the groups R1, R2 and R3 are any of said groups, the third of them is a hydroxy group or a residue of a saturated or unsaturated fatty acid containing 2 to 24 carbon atoms. Other glycerol esters are envisioned, particularly not readily water-soluble glycerides of at least one keto or hydroxy acid, having the formula

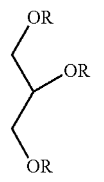

wherein one R group is hydrogen, and two R groups are (—COCH2, COCH3). Additionally, wherein each R is the same or different and is hydrogen, or (—COCH2, COCH3), provided that at least one R is not hydrogen and wherein R' is a linear acid ester of even carbon number from 2 to 20 carbons.

Ketone bodies are used by neurons as a source of Acetyl-CoA. Acetyl-CoA is combined with oxaloacetate to form citrate in the Krebs' cycle, or citric acid cycle (TCA cycle). It is important for neurons to have a source of Acetyl-CoA as well as TCA cycle intermediates to maintain efficient energy metabolism. Yet, neurons lose TCA cycle intermediates to synthesis reactions, such as the formation of glutamate. Neurons also lack pyruvate carboxylase and malic enzyme so they cannot replenish TCA cycle intermediates from. Accordingly, the present disclosure discloses that a combination of ketone bodies with a source of TCA cycle intermediates, in one embodiment. TCA cycle intermediates are selected from a group consisting of citric acid, aconitic acid, isocitric acid, α-ketoglutaric acid, succinic acid, fumaric acid, malic acid, oxaloacetic acid, and mixtures thereof. One embodiment of the disclosure is a combination of TCA cycle intermediates with MCT in a formulation to increase efficiency of the TCA.

Another source of TCA cycle intermediates are compounds that are converted to TCA cycle intermediates within the body (TCA intermediate precursors). Examples of such compounds are 2-keto-4-hydroxypropanol, 2,4-dihydroxybutanol, 2-keto-4-hydroxybutanol, 2,4-dihydroxybutyric acid, 2-keto-4-hydroxybutyric acid, aspartates as well as mono- and di-alkyl oxaloacetates, pyruvate and glucose-6-phosphate.

In certain embodiments, it has been found that additional sources of TCA cycle intermediates and Acetyl-CoA can be advantageously combined with ketone body therapy. Sources of TCA cycle intermediates and Acetyl-CoA include mono- and di-saccharides as well as triglycerides of various chain lengths and structures. Accordingly, in certain aspects, the present disclosure provides that a combination of TCA intermediate precursors with ketone bodies will be beneficial for the treatment of IS and/or the prevention of spasms of IS. For example, the present disclosure discloses that MCT combined with TCA intermediate precursors will be beneficial for the treatment of IS and/or the prevention of spasms of IS.

In other embodiments, further benefit can be derived from formulation of a pharmaceutical composition that includes metabolic adjuvants. Metabolic adjuvants include vitamins, minerals, antioxidants and other related compounds. Such compounds may be chosen from a list that includes but is not limited to; ascorbic acid, biotin, calcitriol, cobalamin, folic acid, niacin, pantothenic acid, pyridoxine, retinol, retinal (retinaldehyde), retinoic acid, riboflavin, thiamin, a-tocopherol, phytylmenaquinone, multiprenylmenaquinone, calcium, magnesium, sodium, aluminum, zinc, potassium, chromium, vanadium, selenium, phosphorous, manganese, iron, fluorine, copper, cobalt, molybdenum, iodine. Accordingly, a combination of ingredients chosen from: metabolic adjuvants, compounds that increase ketone body levels, and TCA cycle intermediates, will prove beneficial for treatment and prevention of diseases of reduced neuronal metabolism, in patients with IS.

In one embodiment, the compositions of the disclosure are administered orally. In another embodiment, the compositions of the disclosure are administered intravenously. Oral administration of MCT and other ketogenic compound preparations as well as intravenous administration are well known to those skilled in the art. In some embodiments, compositions of the disclosure may be in any administratively convenient formulations, including dosage units incorporated into a variety of containers.

In one embodiment, oral and/or intravenous administration of a composition comprising at least one compound capable of elevating ketone body concentrations, such as, for example, MCT or MCFA, result in hyperketonemia. Hyperketonemia, in one embodiment, results in ketone bodies being utilized for energy in the brain even in the presence of glucose.

Convenient unit dosage containers and/or formulations include tablets, capsules, lozenges, troches, hard candies, nutritional bars, nutritional drinks, metered sprays, creams, and suppositories, among others. The compositions may be combined with a pharmaceutically acceptable excipient such as gelatin, oil(s), and/or other pharmaceutically active agent(s). For example, the compositions may be advantageously combined and/or used in combination with other therapeutic or prophylactic agents, different from the subject compounds. In many instances, administration in conjunction with the subject compositions enhances the efficacy of such agents. For example, the compounds may be advantageously used in conjunction with antioxidants, compounds that enhance the efficiency of glucose utilization, and mixtures thereof.

In one embodiment, the subject is intravenously infused with ketogenic compounds such as MCT, MCFA, directly, to a level required to treat and prevent the occurrence of infantile spasms. Preparation of intravenous lipids and ketone body solutions are well known to those skilled in the art.

Effective amounts of dosages of compounds useful in connection with the methods of disclosure, i.e., compounds capable of elevating ketone body concentrations in an amount effective for the treatment of or prevention of infantile spasms, will be apparent to those skilled in the art. Such effective amounts can be determined in light of disclosed blood ketone levels.

In certain embodiments, the daily dose of ketogenic compound used in connection with the methods of the disclosure can be measured in terms of grams of MCT per kg of body weight (BW) of the subject. In some embodiments, the compositions useful in connection with the methods of the disclosure can be administered in the range of about 0.01 g/kg/day to 30 g/kg/day of ketogenic compound.

Where the compound capable of elevating ketone body concentrations is MCT, the MCT dose, in one embodiment, is in the range of about 0.01 g/kg/day to about 30 g/kg/day of MCT. In other embodiments, the dose may be in the range of about 0.05 g/kg/day to about 10 g/kg/day of MCT. In other embodiments, the dose will be in the range of about 0.25 g/kg/day to about 5 g/kg/day of MCT. In other embodiments, the dose will be in the range of about 0.5 g/kg/day to about 2 g/kg/day of MCT. In other embodiments, the dose will be in the range of about 0.1 g/kg/day to about 2 g/kg/day. In other embodiments, the dose of MCT is at least about 0.05 g/kg/day, at least about 0.1 g/kg/day, at least about 0.15 g/kg/day, at least about 0.2 g/kg/day, at least about 0.5 g/kg/day, at least about 1 g/kg/day, at least about 1.5 g/kg/day, at least about 2 g/kg/day, at least about 2.5 g/kg/day, at least about 3 g/kg/day, at least about 4 g/kg/day, at least about 5 g/kg/day, at least about 10 g/kg/day, at least about 15 g/kg/day, at least about 20 g/kg/day, at least about 30 g/kg/day, at least about 40 g/kg/day, and at least about 50 g/kg/day.

In some embodiments, the subject is a mammal, e.g., a human. Other mammals within the scope of this disclosure are mammals such as companion animals, such as a pet or mammal in the care of a human for whether for a long term or briefly. In some embodiments, the companion mammal is a dog or cat.

In another embodiment, the compositions useful in the methods of the disclosure may be a food product or medicinal food formulated specifically for human consumption. Such food compositions may include foods and nutrients intended to supply necessary dietary requirements of a subject, e.g., a human being, as well as other dietary supplements. In one embodiment, the food product or medicinal food is formulated for human consumption, and is complete and nutritionally balanced. In other embodiments, the food product or medicinal food is intended as a nutritional supplements to be used in connection with a well-balanced or formulated diet.

The nutritional supplement may be formulated as drinking water, beverage, liquid concentrate, gel, yoghurt, powder, granule, paste, suspension, chew, morsel, treat, snack, pellet, pill, capsule, tablet, or any other delivery form. The nutritional supplement may be specially formulated for consumption by a particular species or even an individual subject, such as companion animal, or a human. In one embodiment, the nutritional supplement can comprise a relatively concentrated dose of MCT such that the supplement can be administered to the subject in small amounts, or can be diluted before administration to a subject. In some embodiments, the nutritional supplement or other MCT-containing composition may require admixing with water or the like prior to administration to the mammal, for example to adjust the dose, to make it more palatable, or to allow for more frequent administration in smaller doses.

The compositions useful in the methods of the disclosure may be refrigerated or frozen. The ketogenic compound, e.g., MCT, may be pre-blended with the other components of the composition to provide the beneficial amounts needed, may be emulsified, coated onto a food composition, nutritional or dietary supplement, or food product formulated for human or companion animal consumption, or may be added to a composition prior to consuming it or offering it to a subject, for example, using a powder or a mix.

In one embodiment, the compositions comprise a ketogenic compound in an amount effective to treat IS and/or prevent spasms in IS in a subject in need thereof to which the composition has been administered. By way of example, when formulated for human consumption, the amount of ketogenic compound, e.g., MCT, as a percentage of the composition is in the range of about 1% to about 50% of the composition on a dry matter basis, although a lesser or greater percentage can be supplied. In various embodiments, the amount is about 1.0%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%. 30%, 31%, 32%, 33%, 34%, 35%, 36%, 37%, 38%, 39%, 40%, 41%, 42%, 43%, 44%, 45%, 46%, 47%, 48%, 49%, 50% or more, of the composition on a dry weight basis. Nutritional supplements may be formulated to contain several fold higher concentrations of ketogenic compound, e.g., MCT, to be amenable for administration to a subject in the form of a tablet, capsule, liquid concentrated, or other similar dosage form, or to be diluted before administrations, such as by dilution in water, spraying or sprinkling onto a pet food, and other similar modes of administration. For a nutritional or dietary supplement, the ketogenic compound alone may be administered directly to the subject or applied directly to the subject's regular food. Nutritional or dietary supplement formulations in various embodiments contain about 30% to about 100% of the ketogenic compound, although lesser amounts may also used.

In various embodiments, the compositions useful in the methods of the disclosure optionally comprise supplementary substances such as minerals, vitamins, salts, condiments, colorants, and preservatives. Non-limiting examples of supplementary minerals include calcium, phosphorous, potassium, sodium, iron, chloride, boron, copper, zinc, magnesium, manganese, iodine, selenium, and the like. Non-limiting examples of supplementary vitamins include vitamin A, any of the B vitamins, vitamin C, vitamin D, vitamin E, and vitamin K, including various salts, esters, or other derivatives of the foregoing. Additional dietary supplements may also be included, for example, any form of niacin, pantothenic acid, inulin, folic acid, biotin, amino acids, and the like, as well as salts and derivatives thereof. In addition, the compositions may comprise beneficial long chain polyunsaturated fatty acids such as the (n-3) and/or (n-6) fatty acids, arachidonic acid, eicosapentaenoic acid, docosapentaenoic acid, and docosahexaenoic acid, as well combinations thereof.

As described herein, the present disclosure relates to the use of ketogenic compounds, such as MCT or MCFA, in the treatment of infantile spasms and/or the prevention of spasms in infantile spasms. Although the present disclosure contains much specificity, such specificity should not be construed as limiting the scope of the disclosure but merely as providing illustrations for some of the embodiments of this disclosure. For example, administration of ketogenic compounds in accordance with the methods of the disclosure may prove more effective when combined with insulin sensitizing agents such as vanadyl sulfate, chromium picolinate, and vitamin E. Such agents may function to increase glucose utilization and work synergistically with hyperketonemia. In another example ketogenic compounds such as MCT can be combined with compounds that increase the rates of fatty acid utilization. Mixtures of such compounds may synergistically increase levels of circulating ketone bodies.

EXAMPLES

Example 1

Various animal models of IS have been created as tools to test efficacy of various interventions. One such example is a rat triple hit model developed by Scantlebury and co-authors. This model was developed "based on evidence that structural or functional abnormalities in cortical or subcortical structures may be necessary to produce IS." [11]. The model uses three lesions to induce infantile spasms. The lesions include doxorubicin (DOX), lipopolysaccharide (LPS) and p-chlorophenylalanine (PCPA). DOX is an inhibitor of topo isomerase 2 that results in diffuse brain damage involving the forebrain and brainstem when injected intraventricularly. LPS can stimulate the release of inflammatory cytokines in various cell types, leading to an acute inflammatory response. Intracerebral injection of LPS in rat pups activates inflammatory cascades resulting in hypomyelination, white matter rarefaction and necrosis. PCPA depletes serotonin by inhibiting the enzyme tryptophan hydroxylase [11].

In accordance with embodiments of the disclosure, tricaprilin was tested for its ability to reduce spasm frequency in this triple hit model. These studies were done using timed pregnant Sprague Dawley rats. Animals were maintained in a 12 hr light/dark cycle and had free access to food and water. The day of birth was considered as P0. Animal care and use conformed to institutional policy and guidelines of the American Association for the Accreditation of Laboratory Animal Care. All procedures and experiments were performed in accordance with the National Institute of Health Guide for the Care and Use of Laboratory Animals.

At postnatal day (P) 3 DOX (5 μg/2.5 μl) and LPS (3 μg/1.5 μl) were given intracerebrally and at P5 PCPA is given intraperitoneally (i.p.) (200 mg/kg). Intracerebral infusions of DOX and LPS were done stereotaxically under isoflurane anesthesia. Pups were positioned in a stereotaxic frame for neonatal rat surgery (Benchmark Angle One, MyNeurolab.com, St Louis MO). DOX was injected into the right lateral ventricle followed by LPS into the right parietal cortex. Pups were individually placed in beakers warmed in a water bath and filled with bedding (31-33° C.) and fed via a cheek cannula. Spasms begin at day P4 and continue to P13.

Tricaprilin was administered either by oral gavage (administered twice a day), or steadily in milk via the cheek cannula, from P5-P7. Hence, the intervention was post-lesion and post-development of seizures (a treatment paradigm, rather than a preventative paradigm). For gavage, tricaprilin was administered at 5 ml/kg/day and 10 ml/kg/day. When mixed with milk, tricaprilin was administered at 5, 10 and 30 ml/kg/day. Each group comprised 5 animals. Spasms were recorded and scored on P7, urine ketones collected on P7 at 6 and 12 hours after gavage and same timepoints for milk fed pups. The behaviors of the pups were monitored using a video camera for 2 hours twice daily from P4 (first post-operative day) until P20.

Figure 1B:
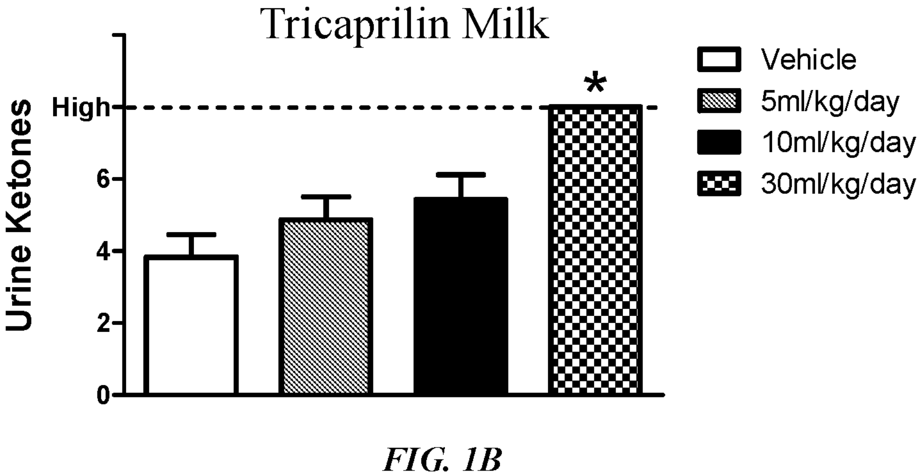

After administration of tricaprilin, urinary ketones were elevated above control levels. With reference to FIG. 1A, the difference in ketone levels at 6 hours post-gavage between Vehicle, 5, and 10 ml/kg/day tricaprilin gavage, calculated as a F-statistic (ratio of mean square values) was statistically significant ($F(2,10)=24.286$, $p<0.001$). Following Tukey post hoc tests, Vehicle treatment was significantly different from the 5 ($p=0.001$), and 10 ($p<0.001$) ml/kg/day doses. The difference in ketone levels at 12 hours post-gavage between Vehicle, 5, and 10 ml/kg/day tricaprilin gavage was also statistically significant ($F(2,10)=21.968$, $p<0.001$). Following Tukey post hoc tests, Vehicle treatment was found to be significantly different from the 5 and 10 ml/kg/day doses (both $p<0.001$). With reference to FIG. 1B, the difference in ketone levels between Vehicle, 5, 10, and 30 ml/kg/day tricaprilin in milk was also statistically significant ($F(3,17)=6.395$, $p=0.004$). Tukey post hoc tests showed significant differences between the 30 ml/kg/day dose with Vehicle treatment ($p=0.003$), as well as with the 5 ml/kg/day dose ($p=0.024$).

Figure 2A:
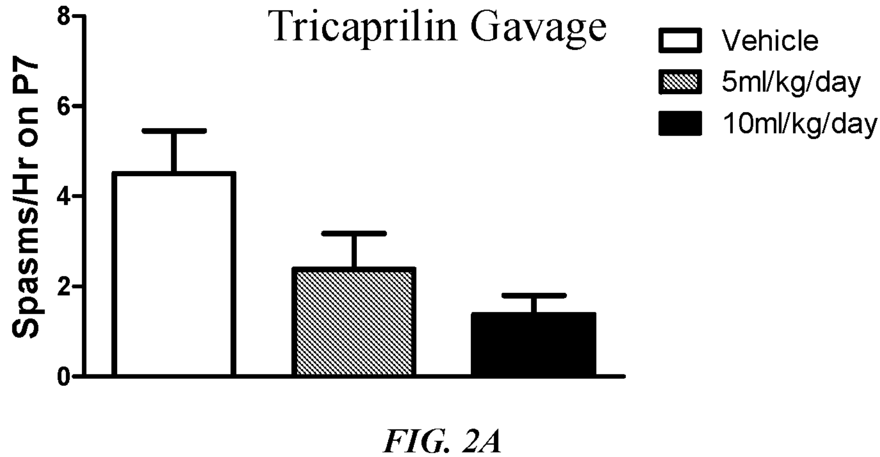
FIGS. 2A and 2B illustrate that tricaprilin reduces spasms in a rat model of IS, after both oral gavage (FIG. 2A) and feeding in milk (FIG. 2B), according to embodiments of the disclosure.
Figure 2B:
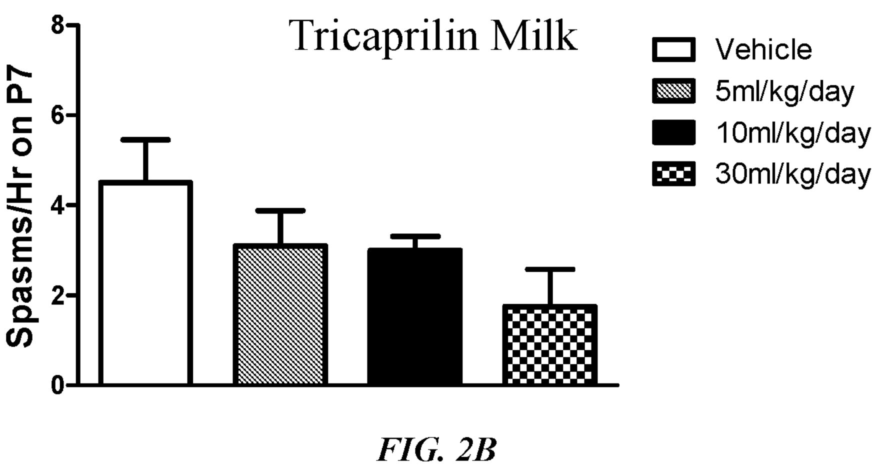

The frequency of spasms varied by concentration of tricaprilin used. Data for vehicle and milk only administration were combined and resulted in a mean 4.5 (SD 2.3) spasms/hour. For oral gavage (FIG. 2A) and when mixed with milk (FIG. 2B), tricaprilin resulted in a reduction in spasms/hr when compared to vehicle. With reference to FIG. 2A, oral gavage of tricaprilin at 5 ml/kg/day resulted in 2.3 spasms/hour (SD 1.6, pvalue 0.155), at 10 ml/kg resulted in 1.4 (SD 0.9, pvalue=0.036). With reference to FIG. 2B, when tricaprilin was mixed with milk at 5 ml/kg/day spasms/hr were 3.1 (SD 1.7, pvalue=0.300), at 10 ml/kg/day 3.0 (SD 0.8, pvalue=0.139), and at 30 ml/kg/day 1.75 (SD 1.7, pvalue 0.079).

In sum, administration of tricaprilin led to an elevation of urinary ketone levels and a reduction in spasms in a triple hit model of IS. Tricaprilin is a ketogenic medium chain triglyceride and administration of MCTs alone may mimic a KD, thus offering the possibility of an effective therapeutic.

Example 2

In this phase I, pilot, open-label study with infants, subjects will be selected based on their lack of response to first line treatments (ACTH/prednisolone and vigabatrin). The study will use a dose of tricaprilin based on data from use of non-drug formulations of MCTs and KDs in IS. The dose will be escalated gradually, and safety and tolerability will be monitored along with effects on clinical spasm activity and EEG activity via 24 hr vEEG recording and caregiver spasm/seizure diaries.

This study will provide safety and tolerability information as well as preliminary efficacy data on the use of tricaprilin in infants with IS.

Approximately 30 subjects will be screened to achieve up to a maximum of 10 evaluable subjects. Subjects are eligible to be included in the study only if all of the following criteria apply:

Age & Sex

Male and female infants ages 3 months to 24 months, inclusive, at the time of parent/legal guardian signing the informed consent Type of Subject and Disease Characteristics Clinical diagnosis of IS, confirmed by analysis of a 24-hour vEEG recording, including at least one documented spasm Continued infantile spasms despite adequate treatment with oral prednisolone (or ACTH) and vigabatrin Subjects must have tried treatment and failed; or parents/legal guardians have refused treatment with prednisolone/ACTH and vigabatrin; or there is a contraindication to use of these classes of agents If being treated with concomitant anti-seizure drugs (ASDs) other than ketogenic therapies/diet Current ASDs have been at a constant daily dose for at least 1 week; Note: At the discretion of the Investigator and medical monitor, subjects with minor dose adjustments may be allowed to enter the study sooner than 1 week following the adjustment.

Subject is taking no more than 3 concomitant ASDs

Body weight within 2 standard deviations of the mean weight for their age

Parent(s)/legal guardian(s) has read and voluntarily signed the informed consent form (ICF) approved by an Independent Ethics Committee (IEC) and agrees to compliance with the requirements and restrictions listed in this protocol 5.2. Exclusion Criteria Subjects are excluded from the study if any of the following criteria apply:

Subject considered by the Investigator, for any reason, to be an unsuitable candidate to receive the investigational product Significant and active pre-existing cardiovascular, renal, liver, infectious, or other systemic disease Subject has clinically significant renal impairment, defined as creatinine >1.5 mg/dL or blood urea nitrogen >2×upper limit of normal (ULN); clinically significant liver dysfunction, defined as total bilirubin ≥2×ULN, or aspartate aminotransferase or alanine aminotransferase ≥3×ULN; or has clinically significant abnormal laboratory values. The Investigator may deem the subject eligible, however, if he/she judges the laboratory values to be not clinically significant.

Clinically significant abnormality on ECG that, in the opinion of the Investigator, increases the safety risks of participating in the study Known or suspected allergy to the investigational product Known history of aspiration pneumonia within the past year Previous participation in another clinical study of the investigational product or received any investigational drug, device, or therapy within 30 days of study entry or within five half-lives of another investigational drug Within 14 days of screening, subject has:

received therapy with felbamate, cannabinoids, ketogenic diet or vagus nerve stimulation received therapy with ACTH, prednisolone or other steroid Pre-existing lethal or potentially lethal condition other than infantile spasms with a significant risk of death before 18 months of age such as non-ketotic hyperglycinemia Previous failure to respond to an appropriate trial (at least 2 weeks) of the ketogenic diet Subjects will start on a dose equal to 5% of their daily caloric intake based on weight, spread over 4 doses per day, approximately 6 hours apart. The dose can be administered with feeds or at other times.

Subjects will titrate over 5-14 days to a dose which leads to adequate control of spasms/seizures based on the investigator's judgement, so long as the IMP remains well tolerated. Dose will not be increased beyond the point where 60% of daily caloric intake is provided by tricaprilin, or up to a predefined maximum of 10 g/kg/day.

| Day | Percentage of daily calories from IMP |
|---|---|
| 1 | 5 |
| 2 | 10 |
| 3 | 20 |
| 4 | 30 |
| 5 | 40 |
| 6 | 40 |
| 7* | 50 |
| 8 | 50 |
| 9* | 60 |

*escalation of dosing beyond 40% of total daily calories provided by tricaprilin, should only be done, if the IMP is well tolerated and after adjustment of the diet by the site dietician, and if further increase is in the interest of the infant, according to investigator's judgement The required volume of tricaprilin will be aspirated from the bottle by affixing a single-use syringe to the syringe adaptor and inverting the bottle.

The tricaprilin will be emulsified in a blender with infant formula/milk/breast milk (see IMP Manual for volume and method details) and administered to the infant.

Detailed instructions, individualised per subject based on the subject's age, body weight, and nutritional needs will be provided to the parent/legal guardian. The subject's parent/legal guardian will be advised to decrease the amount of regular feed, as necessary, such that subject's total daily intake remains isocaloric. Specific instructions will be provided to parents/legal guardians for each child, at each dosing level, and if necessary nutritional supplements will be provided to maintain nutritional balance.

Study Outcomes

Seizure/Spasm Diary

A seizure/spasm record in the Caregiver Diary will be completed by the subject's parent(s)/legal guardian(s) each day for the duration of the study to include a count of all spasm and seizure activity observed that day. The seizure/spasm record in the Caregiver Diary will be reviewed at each in-clinic visit and collected by study staff at Follow-up (Visit 6) or Withdrawal Visit.

Behavioural Questionnaires

Parent(s)/Legal guardian(s) will complete 5 questions on the subject's crying and sleep (less than usual, usual, more than usual), awakeness/alertness (worse than usual, usual, better than usual), fussiness (not fussy, mildly fussy, moderately fussy, very fussy), and overall rating on how the subject's day was (good, so-so, bad, nightmare).

Brussels Infant and Toddler Stool Scale Diary

Parent(s)/Legal guardian(s) will complete the Brussels Infant and Toddler Stool Scale[14] record in the Caregiver Diary daily. The diary will collect, for each stool passed by the infant, the time and a consistency rating; hard, formed, loose, or watery.

24-Hour Video-Electroencephalogram (vEEG)

A 24-hour vEEG will be performed at Visit 1 for a baseline measurement. If the subject is not showing clinical benefit at the end of the Titration Period, a vEEG will be done at Visit 4. All subjects who enter the the Maintenance Period, will have another vEEG (which may be their second or third vEEG of the study) at the end of the Maintenance Period (Visit 5).

Caregiver and Clinical Global Impression of Change (CaGIC, CGIC)

The Caregiver Global Impression of Change (CaGIC) is a single-question assessment completed by the parent(s)/legal guardian(s). The question assesses the status of the subject's condition since treatment start. The parent/legal guardian provides a rating on a 7-point scale from 1 (very much improved) to 7 (very much worse).

The Clinical Global Impression of Change (CGIC) is a single-question assessment completed by the Investigator. The question assesses the status of the subject's condition since treatment start. The Investigator provides a rating on a 7-point scale from 1 (very much improved) to 7 (very much worse).

Vineland Assessment

The Vineland Adaptive Behavior Scales Third Edition (Vineland-3)'[5] is designed to assess intellectual and developmental disabilities. This assessment will be completed by the Investigator or delegate on Visits 2, 4, and 5.

Urine Ketone Assessment

Urine ketone assessments will be performed daily throughout the Baseline, Titration, and Maintenance periods. Urine ketone testing strips will be used. Urine is to be collected using a cotton ball placed in the subject's diaper. The cotton ball is then squeezed over the urine ketone testing strip and the result captured in the Caregiver Diary.

Outcomes

Primary Objectives are to determine the safety and tolerability of daily administration of tricaprilin in subjects with Infantile Spasms (IS) by measuring endpoints in:

Adverse events
Vital signs
Laboratory tests
Brussels Infant and Toddler Stool Scale Secondary Objectives are to:

1. Determine the efficacy of daily administration of tricaprilin in subjects with Infantile Spasms on spasm frequency (clinical) by measuring endpoints in:
2. Change in spasm frequency, as measured by the number of clusters and the mean cluster duration based on Caregiver's Diary, at the end of the treatment period (1-week period) as compared to baseline (1-week period) and by the number and percentage of subjects spasm-free and seizure-free (showing no seizure activity of any type, IS or otherwise) for at least 48 hours (clinical diary response).
3. To determine the efficacy of daily administration of tricaprilin in subjects with Infantile Spasms on spasm frequency (vEEG) by measuring: Change in spasm frequency, as measured by: the number of clusters, the mean cluster duration based on a 24-hour video-EEG (vEEG) at the end of the treatment period as compared to the final 24 hours of the baseline period. Change in all seizure frequency, as measured by a vEEG at the end of the treatment period as compared to the final 24 hours of the baseline period. The number and percentage of participants spasm-free and seizure-free (showing no seizure activity of any type, IS or otherwise) for at least 24 hours at the end of each period (Electroclinical response), based on video seizure counts and 24 h vEEG. The number and percentage of responders (>25%, 50%, 75% decrease in spasm frequency) based on the 24-hour vEEG at the end of the treatment period
4. To assess tolerability of daily administration of tricaprilin by measuring change from baseline in behavioural questionnaires.

Exploratory objectives are to

1. Explore possible relationship between ketone levels and markers of clinical outcomes by measuring relationships between blood ketone levels and: Spasm and seizure frequency (including any type of seizure, IS or other); Hypsarrhythmia and other vEEG changes; Measures of safety
2. Explore effect of tricaprilin administration on drug level(s) of concomitant ASD by measuring concomitant ASD drug level(s)
3. Exploratory potential predictors of clinical outcomes by measuring: Relationships between clinical outcomes and baseline measures such as: Type of IS: Cryptogenic or symptomatic; Age of onset of spasms; Treatment lag: time between onset of spasms and initiation of treatment; Occurrence of non-spasm seizure types.
4. Explore efficacy of daily administration of tricaprilin in subjects with Infantile Spasms on spasm frequency (vEEG) by measuring Change in frequency of hypsarrhythmia, as determined by the Burden of Amplitudes and Epileptiform Discharges (BASED) scale score.
5. To determine the efficacy of daily administration of tricaprilin in subjects with IS on global impression of change by measuring: Caregiver Global Impression of Change (CaGIC) score at the end of treatment; Clinical Global Impression of Change (CGIC).

Any ranges cited herein are inclusive. The terms "substantially" and "about" used throughout this disclosure are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the method and system, which, as a matter of language, might be said to fall therebetween.

Any ranges cited herein are inclusive. The terms "substantially" and "about" used throughout this disclosure are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the method and system, which, as a matter of language, might be said to fall therebetween.

REFERENCES

1. Wheless, J. W., et al., *Infantile spasms (West syndrome): update and resources for pediatricians and providers to share with parents*. BMC Pediatr, 2012. 12: p. 108.
2. Kellaway, P., et al., *Precise characterization and quantification of infantile spasms*. Ann Neurol, 1979. 6(3): p. 214-8.
3. Riikonen, R., *Long-term outcome of West syndrome: a study of adults with a history of infantile spasms*. Epilepsia, 1996. 37(4): p. 367-72.
4. Watanabe, K., *West syndrome: etiological and prognostic aspects*. Brain Dev, 1998.
5. Marshall, C. R., et al., *Infantile spasms is associated with deletion of the MAGI2 gene on chromosome 7q11.23-q21.11*. Am J Hum Genet, 2008. 83(1): p. 106-11.
6. Michaud, J. L., et al., *The genetic landscape of infantile spasms*. Hum Mol Genet, 2014. 23(18): p. 4846-58.
7. Zhongshu, Z., et al., *Clinical analysis of West syndrome associated with phenylketonuria*. Brain Dev, 2001. 23(7): p. 552-7.
8. Smith, M. S., R. Matthews, and P. Mukherji, *Infantile Spasms*, in *StatPearls*. 2020: Treasure Island (FL).
9. Stafstrom, C. E. and G. L. *Holmes, Infantile spasms: criteria for an animal model*. Int Rev Neurobiol, 2002. 49: p. 391-411.
10. Pellock, J. M., et al., *Infantile spasms: a U.S. consensus report*. Epilepsia, 2010. 51(10): p. 2175-89.
11. Scantlebury, M. H., et al., *A model of symptomatic infantile spasms syndrome*. Neurobiol Dis, 2010. 37(3): p. 604-12.
12. Cortez, M. A., et al., *Infantile spasms and Down syndrome: a new animal model*. Pediatr Res, 2009. 65(5): p. 499-503.
13. Baram, T. Z., et al., *High-dose corticotropin (ACTH) versus prednisone for infantile spasms: a prospective, randomized, blinded study*. Pediatrics, 1996. 97(3): p. 375-9.
14. Mackay, M. T., et al., *Practice parameter: medical treatment of infantile spasms: report of the American Academy of Neurology and the Child Neurology Society*. Neurology, 2004. 62(10): p. 1668-81.
15. Prezioso, G., et al., *Efficacy of ketogenic diet for infantile spasms: A systematic review*. Acta Neurol Scand, 2018. 137(1): p. 4-11.
16. Hrachovy, R. A., J. D. Frost, Jr., and D. G. Glaze, *High-dose, long-duration versus low-dose, short-duration corticotropin therapy for infantile spasms*. J Pediatr, 1994. 124(5 Pt 1): p. 803-6.
17. Lux, A. L., et al., *The United Kingdom Infantile Spasms Study comparing vigabatrin with prednisolone or tetracosactide at 14 days: a multicentre, randomised controlled trial*. Lancet, 2004. 364(9447): p. 1773-8.
18. Elterman, R. D., et al., *Randomized trial of vigabatrin in patients with infantile spasms*. Neurology, 2001. 57(8): p. 1416-21.
19. Hrachovy, R. A., et al., *Double-blind study of ACTH vs prednisone therapy in infantile spasms*. J Pediatr, 1983. 103(4): p. 641-5.
20. Eun, S. H., et al., *Ketogenic diet for treatment of infantile spasms*. Brain Dev, 2006. 28(9): p. 566-71.
21. Kossoff, E. H., et al., *A case-control evaluation of the ketogenic diet versus ACTH for new-onset infantile spasms*. Epilepsia, 2008. 49(9): p. 1504-9.
22. Hong, A. M., et al., *Infantile spasms treated with the ketogenic diet: prospective single-center experience in 104 consecutive infants*. Epilepsia, 2010. 51(8): p. 1403-7.
23. Caraballo, R., et al., *Long-term follow-up of the ketogenic diet for refractory epilepsy: multicenter Argentinean experience in 216 pediatric patients*. Seizure, 2011. 20(8): p. 640-5.
24. Numis, A. L., et al., *The relationship of ketosis and growth to the efficacy of the ketogenic diet in infantile spasms*. Epilepsy Res, 2011. 96(1-2): p. 172-5.
25. Li, B., et al., *Effects of ketogenic diet on the clinical and electroencephalographic features of children with drug therapy-resistant epilepsy*. Exp Ther Med, 2013. 5(2): p. 611-615.
26. Lee, J., et al., *Prognostic factors of infantile spasms: role of treatment options including a ketogenic diet*. Brain Dev, 2013. 35(8): p. 821-6.
27. Pires, M. E., et al., *Ketogenic diet for infantile spasms refractory to first-line treatments: an open prospective study*. Epilepsy Res, 2013. 105(1-2): p. 189-94.
28. Kayyali, H. R., et al., *Ketogenic diet efficacy in the treatment of intractable epileptic spasms*. Pediatr Neurol, 2014. 50(3): p. 224-7.
29. Hirano, Y., et al., *Ketogenic diet therapy can improve ACTH-resistant West syndrome in Japan*. Brain Dev, 2015. 37(1): p. 18-22.
30. Hussain, S. A., et al., *Limited efficacy of the ketogenic diet in the treatment of highly refractory epileptic spasms*. Seizure, 2016. 35: p. 59-64.
31. O'Callaghan, F. J., et al., *The effect of lead time to treatment and of age of onset on developmental outcome at 4 years in infantile spasms: evidence from the United Kingdom Infantile Spasms Study*. Epilepsia, 2011. 52(7): p. 1359-64.
32. Go, C. Y., et al., *Evidence-based guideline update: medical treatment of infantile spasms. Report of the Guideline Development Subcommittee of the American Academy of Neurology and the Practice Committee of the Child Neurology Society*. Neurology, 2012. 78(24): p. 1974-80.
33. Groleau, V., et al., *Long-term impact of the ketogenic diet on growth and resting energy expenditure in children with intractable epilepsy*. Dev Med Child Neurol, 2014. 56(9): p. 898-904.
34. Shaw, D. M., et al., *Exogenous Ketone Supplementation and Keto-Adaptation for Endurance Performance: Disentangling the Effects of Two Distinct Metabolic States. Sports Med,* 2020. 50(4): p. 641-656.
35. Poff, A. M., A. P. Koutnik, and B. Egan, *Nutritional Ketosis with Ketogenic Diets or Exogenous Ketones: Features, Convergence, and Divergence*. Curr Sports Med Rep, 2020. 19(7): p. 251-259.
36. Sharman, M. J., et al., *A ketogenic diet favorably affects serum biomarkers for cardiovascular disease in normal-weight men*. J Nutr, 2002. 132(7): p. 1879-85.

What is claimed is:

1. A method for the treatment of Infantile Spasms and/or the prevention of spasms of Infantile Spasms in a subject in need thereof, the method comprising: administering an effective amount of a composition comprising tricaprilin, wherein the tricaprilin is capable of elevating ketone body concentrations in the body of the subject.

2. The method of claim 1, wherein the composition is an emulsion.

3. The method of claim 1, wherein greater than 95% of the fatty acids of the tricaprilin are octanoic acid comprised of 8 carbons (C8).

4. The method of claim 1, wherein the composition is administered in an amount effective to treat Infantile Spasms in the subject.

5. The method of claim 1, wherein the composition is administered in an amount effective to reduce spasms of Infantile Spasm in the subject by at least 50%, when compared to no treatment.

6. The method of claim 1, wherein the composition is administered in an amount effective to reduce spasms of Infantile Spasm in the subject by at least 75%, when compared to no treatment.

7. The method of claim 1, wherein the composition is administered orally or intravenously.

8. The method of claim 1, wherein the composition is administered orally as a nutritional supplement.

9. The method of claim 1, wherein the tricaprilin is administered in an amount ranging from about 0.01 g/kg/day to about 30 g/kg/day in the composition.

10. The method of claim 1, wherein the tricaprilin is administered in an amount ranging from about 0.05 g/kg/day to about 20 g/kg/day in the composition.

11. The method of claim 1, wherein the composition is administered in single or divided doses.

12. The method of claim 1, wherein the composition is administered once, twice, or three times daily.

13. The method of claim 1, wherein the subject is a human.

* * * * *